Figure 1:
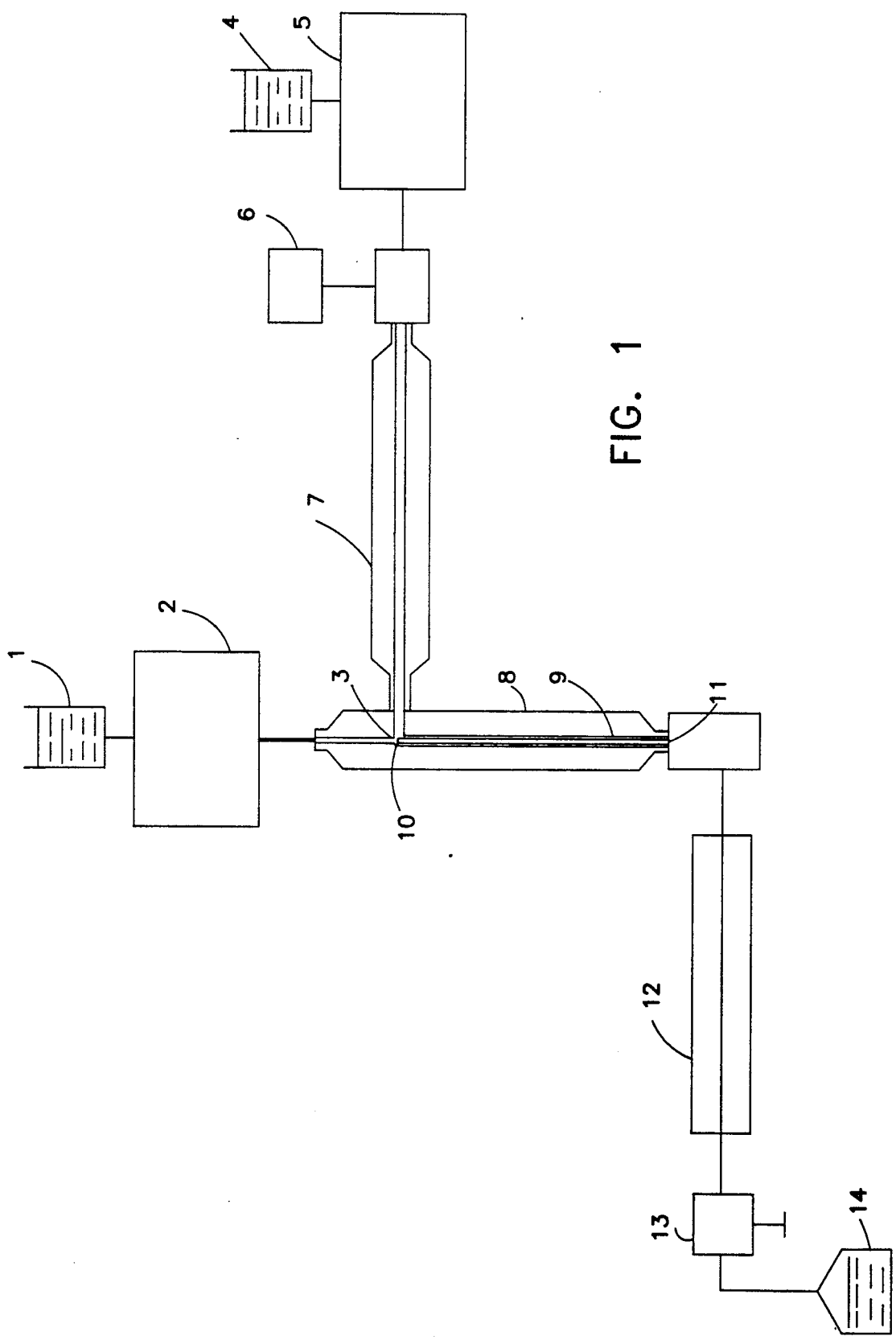

United States Patent [19]

Buback et al.

[11] Patent Number: 5,151,533
[45] Date of Patent: Sep. 29, 1992

[54] PROCESS FOR THE PRODUCTION OF 3-HYDROXY-1,3,5(10)-ESTRATRIEN-17-ONE

[75] Inventors: Michael Buback, Gottingen; Josef Hader, Berlin; Hans-Peter Voegele; ZaKarya Al-Massri, both of Göttingen, all of Fed. Rep. of Germany

[73] Assignee: Schering Aktiengesellschaft, Berlin and Bergkamen, Japan

[21] Appl. No.: 721,608
[22] PCT Filed: Sep. 6, 1990
[86] PCT No.: PCT/DE90/00690
 § 371 Date: Jun. 22, 1991
 § 102(e) Date: Jun. 22, 1991
[87] PCT Pub. No.: WO91/04264
 PCT Pub. Date: Apr. 4, 1991

[30] Foreign Application Priority Data

Sep. 20, 1989 [DE] Fed. Rep. of Germany ....... 3931820

[51] Int. Cl.$^5$ ................................................. C07J 1/00
[52] U.S. Cl. .................................... 552/625; 552/630
[58] Field of Search ................. 552/625, 630; 568/799

[56] References Cited

FOREIGN PATENT DOCUMENTS 2537254 8/1975 Fed. Rep. of Germany .

Primary Examiner—Alan Siegel
Assistant Examiner—Kimberly J. Kestler

[57] ABSTRACT

A process for the production of 3-hydroxy-1,3,5(10)-estratrien-17-one by pyrolysis of 1,4-androstadiene-3,17-dione in the presence of 1,2,3,4-tetrahydronaphthalene as hydrogen donor is described, by 1,2,3,4-tetrahydronaphthalene, preheated to a temperature of 450°–850° C., in a mixing zone being mixed with a solution, heated to a temperature of up to 300° C., of 1,4-androstadiene-3,17-dione, in 1,2,3,4-tetrahydronaphthalene, the mixture being heated in a pyrolysis zone at a retention time of 0.001 to 60 seconds to temperatures of 450°–700° C. and the product leaving the pyrolysis zone being cooled off, which is characterized in that the pyrolysis is performed under a pressure of $3.5 \times 10^6$ to $3 \times 10^8$ Pa.

6 Claims, 2 Drawing Sheets

PROCESS FOR THE PRODUCTION OF 3-HYDROXY-1,3,5(10)-ESTRATRIEN-17-ONE

SUMMARY OF THE INVENTION

The invention relates to a process for the production of 3-hydroxy-1,3,5(10)-estratrien-17-one (=estrone) as well as a device for performing this process.

From German patent specification 25 37 254, a process for the production of 3-hydroxy-1,3,5(10)-estratrien-17-one by pyrolysis of 1,4-androstadiene-3,17-dione in the presence of hydrocarbons as hydrogen donors is previously known whose features are that a hydrocarbon, preheated to a temperature of 450°–850° C., in a mixing zone is mixed in a hydrocarbon, with a solution of 1,4-androstadiene-3,17-dione, heated to a temperature of up to 300° C., the reaction gas is heated in a pyrolysis zone at a retention time of 0.001 to 60 seconds to temperatures of 450°–700° C. and the product leaving the pyrolysis zone is cooled off. In the embodiments of this patent specification, it is mentioned that 1,2,3,4-tetrahydronaphthalene can also be used as hydrocarbon, and that the reaction can be performed under a pressure of up to $3 \times 10^6$ Pa.

The most significant drawback of this previously known process is to be seen in that the pyrolysis zone is quickly clogged by the formation of tar and soot in the performance of the process and the frequently, necessary cleaning of this zone impedes a performance of the process which is acceptable under economic conditions. In addition in the previously known processes, in which the reaction is performed in the gas phase, only a relatively low space-time yield of process product is obtained.

It has now been found that this drawback of the previously known process surprisingly can be avoided, if the pyrolysis is performed under a pressure of $3.5 \times 10^6 - 3 \times 10^8$ Pa.

Under these conditions of the process according to the invention, surprisingly high yields of process product are also achieved, overheating is avoided and a high space-time yield of process product is obtained.

The process according to the invention is performed under conditions in which both the critical temperature of 1,2,3,4-tetrahydronaphthalene of 446° C. and its critical pressure of about $3.5 \times 10^6$ Pa is exceeded, so that the reaction is performed in a supercritical fluid phase.

The process according to the invention can be performed in the devices which are described in German patent specification 25 37 254, provided that they have suitable dimensions and are manufactured from a material which withstands a pressure of $3.5 \times 10^6$ Pa to $3 \times 10^8$ Pa and that it contains a valve between the heat exchanger and the collecting vessel which guarantees the maintenance of the desired pressure in the pyrolysis zone.

A very suitable, sturdy and simple device is represented in attached FIG. 1. It is manufactured basically of stainless steel.

From a storage vessel 1, which contains the solution of 1,4-androstadiene-3,17-dione in 1,2,3,4-tetrahydronaphthalene, the latter is fed by a pump 2 in mixing zone 3. Simultaneously, 1,2,3,4-tetrahydronaphthalene is guided from a second storage vessel 4 by a pump 5 through a preheating cell 7 provided with a pressure guage and after reaching the desired temperature it is also fed into mixing zone 3. Mixing zone 3 is itself in the head of electrically heatable pyrolysis reactor 8, which contains a 130 mm long annular gap 9 of a 4.5 mm outer diameter and a 4.2 mm inner diameter. A thermocouple element 10 and 11 is respectively placed at the head of the annular gap and at its end.

After leaving the pyrolysis reactor, the reaction mixture is cooled in a cooling device 12 gets into collecting tank 14 by a valve 13, which guarantees the maintenance of the desired pressure in the pyrolysis zone.

It is obvious to one skilled in the art that this device can be modified according to the requirements. Thus, the device can be provided, for example, with an additional preheating cell, which also makes it possible to heat the solution of 1,4-androstadiene-3,17-dione in 1,2,3,4-tetrahydronaphthalene before it is fed into mixing zone 3. But on the other hand, it is also possible, for example, to change the annular gap diameter and/or the annular gap length. An increase of the annular gap diameter has the advantage that the flow rate of the reaction mixture is considerably increased.

The yields achievable by the process according to the invention are decisively dependent on the reaction temperature in the pyrolysis zone (450° C.–700° C.; preferably 540° C. to 650° C.) and the retention time of the reaction mixture in the pyrolysis zone. This time is generally only about 0.1 second to about 3 seconds. Too long a retention time is disadvantageous, since the formed estrone is cleaved pyrolytically. Exact adherence to the optimal reaction time in the pyrolysis zone is decisively dependent on how quickly the desired reaction temperature of the 1,4-androstadiene-3,17-dione to be reacted can be reached. This temperature can obviously be reached all the more quickly the larger the ratio of the preheated 1,2,3,4-tetrahydronaphthalene to the 1,4-androstadiene-3,17-dione solution is. The larger this ratio is, on the other hand, the more disadvantageous the economic feasibility of the process is, since the space-time yield of process product decreases accordingly. According to our tests, it has proven advisable to use 2 to 10 volume units of preheated 1,2,3,4-tetrahydronaphthalene per volume unit of 1,4-androstadiene-3,17-dione solution. It is obvious to one skilled in the art that the desired reaction temperature in the pyrolysis zone is reached all the more quickly the more concentrated the 1,4-androstadiene-3,17-dione solution is and the higher the latter was preheated. In the case of 1,4-androstadiene-3,17-dione solutions, which are not preheated, it is advisable according to our tests to use those which contain about 20 to 100 g of 1,4-androstadiene-3,17-dione per 1,000 ml of 1,2,3,4-tetrahydronaphthalene. Our tests with preheated 1,4-androstadiene-3,17-dione solution have not yet been performed.

To achieve optimal yields, it is also important that the reaction mixture is cooled off after the reaction has been completed.

According to the invention, the pyrolysis is performed under a pressure of $3.5 \times 10^6$ to $3 \times 10^8$ Pa and in particular under a pressure of $5 \times 10^6$ to $2 \times 10^7$ Pa. The use of still higher pressures seems to provide no advantages, but on the contrary it could be so that the formation of by-products is somewhat increased by the use of a very high pressure. In addition the technical performance of the process is all the more expensive with regard to the apparatus, in which the process is performed, the higher the pressure is.

The following embodiment is used to explain the invention in more detail.

EXAMPLE

The already-described device is used for performing the process.

From storage vessel (4), 30 ml of 1,2,3,4-tetrahydronaphthalene per minute is introduced by pump (5) in preheating cell (7), where it is heated to a temperature which is about 50° C. above the reaction temperature desired finally and then it is fed into mixing zone (3) of pyrolysis reactor (8) heated to the desired reaction temperature. Simultaneously, 10 ml of solution per minute is fed by pump (2) into mixing zone (3) of pyrolysis reactor (8) from storage vessel (1), which contains a solution of 50 g of 1,4-androstadiene-3,17-dione in 1,000 ml of 1,2,3,4-tetrahydronaphthalene.

After flowing through annular gap (9), the reaction mixture is cooled in cooling device (12) and gets into collecting tank (14) by valve (13), which is used to adjust the desired reaction pressure.

Samples of the reaction mixture are analyzed by gas-chromatographic analysis for their 1,4-androstadiene-3,17-dione and estrone content.

The following three relations are determined from measurements at different temperatures and different pressures:

1. For the first order velocity coefficients of the ADD decomposition, the relation $$\ln (k_{ADD}s^{-1}) = 37.5 - 29762/T$$

(ADD = 1,4-androstadiene-3,17-dione)

2. For the selectivity of the ADD decomposition in estrone, the relation:

$$\ln (\% \ OES/\% \ NPR) = 22.5 - 17\ 391/T$$

(OES = estrone; NPR = byproducts)

3. For the first order velocity coefficients of the decompostion of estrone, the relation $$\ln (k_{oes}s^{-1}) = 21.3 - 19820/T$$

(The temperatures in the preceding formulas are to be given in Kelvin in each case.)

Figure 2:
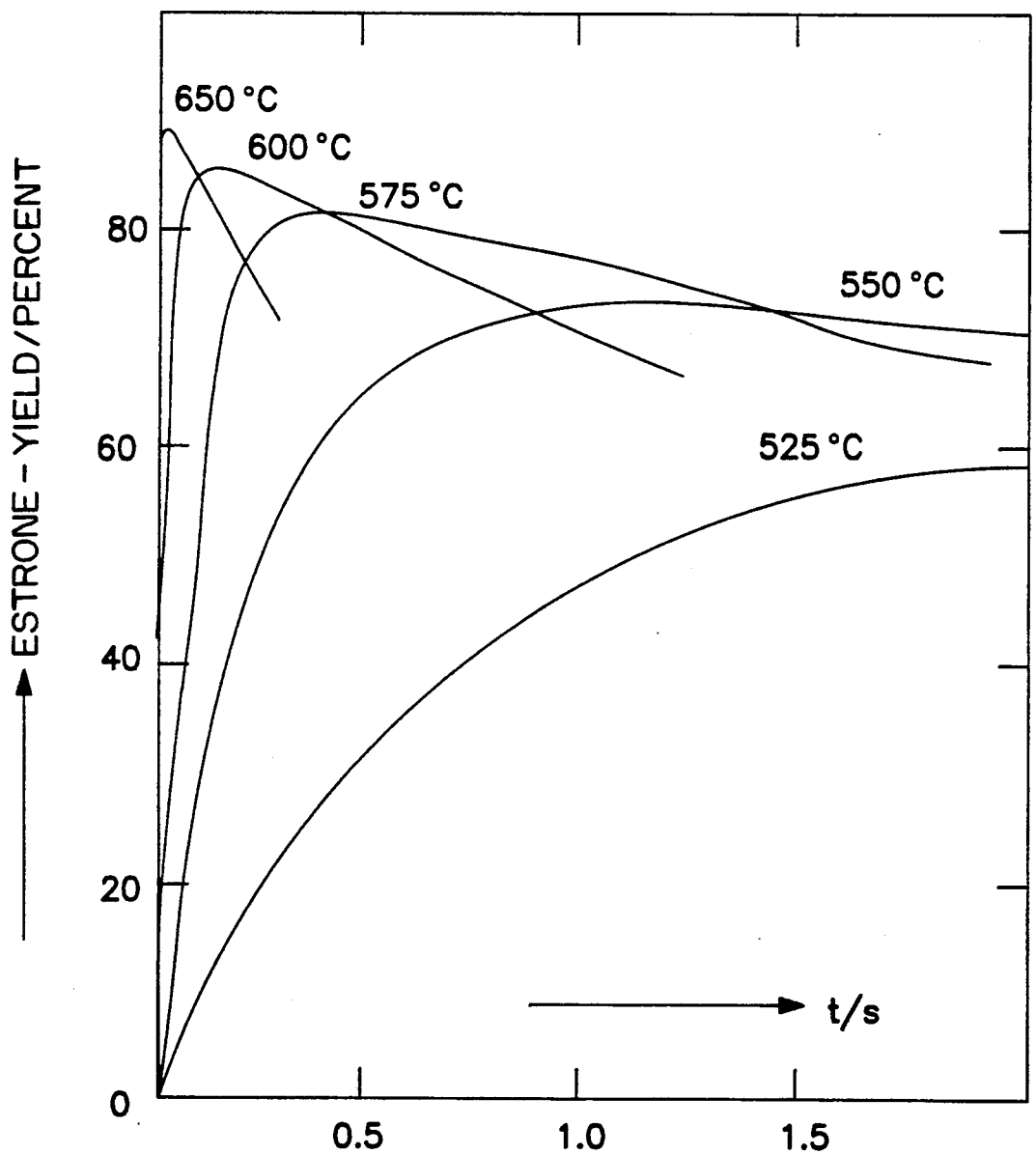

From these relations, the yields of estrone (OES) represented in FIG. 2 are shown to be a function of the reaction time and the reaction temperature.

FIG. 2 Key: OES—Ausbeute/Prozent=Estrone—Yield/Percent.

We claim:

1. A process for the production of 3-hydroxy-1,3,5(10)-estratrien-17-one by pyrolysis of 1,4-androstadiene-3,17-dione in the presence of 1,2,3,4-tetrahydronaphthalene as hydrogen donor, comprising:

preheating 1,2,3,4-tetrahydronaphthalene to a temperature of 450°–480° C.;

mixing the preheated 1,2,3,4-tetrahydronaphthalene in a mixing zone with a solution of 1,4-androstadiene-3,17-dione, in 1,2,3,4-tetrahydronaphthalene, said solution being heated to a temperature of up to 300° C.;

heating the resultant mixture in a pyrolysis zone to a temperature of 450°–700° C., under a pressure of $3.5 \times 10^6 - 3 \times 10^8$ Pa, and a retention time of 0.001 to 60 seconds; and removing the resultant product from said pyrolysis zone and cooling same.

2. A process according to claim 1, wherein said pyrolysis zone is heated to a temperature of 540°–650° C.

3. A process according to claim 1, wherein said retention time is 0.1–3 seconds.

4. A process according to claim 1, wherein said mixture contains 2–10 volume units of preheated 1,2,3,4-tetrahydronaphthalene per volume of 1,4-androstadiene-3,17-dione solution.

5. A process according to claim 1, wherein said pressure in said pyrolysis zone is $5 \times 10^6 - 2 \times 10^7$ Pa.

6. A process according to claim 1, wherein said solution contains 20–100 g of 1,4androstadiene-3,17-dione per 100 ml of 1,2,3,4-tetrahydronaphthalene.

* * * * *

UNITED STATES PATENT AND TRADEMARK OFFICE
CERTIFICATE OF CORRECTION

PATENT NO. : 5,151,533
DATED : September 29, 1992
INVENTOR(S) : Michael BUBACK et al.

It is certified that error appears in the above-identified patent and that said Letters Patent is hereby corrected as shown below:

Claim 6; Col. 4; Line 40: delete "100" and insert --1000--

Signed and Sealed this

Seventh Day of September, 1993

Attest:

BRUCE LEHMAN

Attesting Officer

Commissioner of Patents and Trademarks